United States Patent [19]

Swartz et al.

[11] Patent Number: 5,840,027
[45] Date of Patent: Nov. 24, 1998

[54] GUIDING INTRODUCER SYSTEM FOR USE IN THE RIGHT ATRIUM

[75] Inventors: John F. Swartz, Tulsa, Okla.; John D. Ockuly; John J. Fleischhacker, both of Minnetonka, Minn.; James A. Hassett, Bloomington, Minn.

[73] Assignee: Daig Corporation, Minnetonka, Minn.

[21] Appl. No.: 681,669

[22] Filed: Jul. 29, 1996

Related U.S. Application Data

[60] Division of Ser. No. 333,759, Nov. 3, 1994, Pat. No. 5,628,316, which is a continuation-in-part of Ser. No. 146,744, Nov. 3, 1993, Pat. No. 5,427,119.

[51] Int. Cl.$^6$ ........................................................ A61B 5/00
[52] U.S. Cl. ............................. 600/433; 600/434; 604/95; 604/280
[58] Field of Search ..................................... 128/772, 657, 128/658; 604/95, 96, 280, 281, 282, 283

[56] References Cited

U.S. PATENT DOCUMENTS

| | | |
|---|---|---|
| 4,033,331 | 7/1977 | Guss et al. . |
| 4,117,836 | 10/1978 | Erikson . |
| 4,581,017 | 4/1986 | Sahota ..................................... 604/101 |
| 4,641,649 | 2/1987 | Walinsky et al. . |
| 4,785,815 | 11/1988 | Cohen ..................................... 128/642 |
| 4,882,777 | 11/1989 | Narula . |
| 4,883,058 | 11/1989 | Ruiz . |
| 4,898,591 | 2/1990 | Jang et al. . |
| 4,945,912 | 8/1990 | Langberg . |
| 5,016,640 | 5/1991 | Ruiz . |
| 5,147,336 | 9/1992 | Wendell et al. ......................... 604/283 |
| 5,215,540 | 6/1993 | Anderhub . |
| 5,231,994 | 8/1993 | Harmjanz . |
| 5,242,441 | 9/1993 | Avitall . |
| 5,476,495 | 12/1995 | Kordis et al. . |

OTHER PUBLICATIONS

Feld, Gregory K. Radio frequency Catheter Ablation of Cardiac Arrhythmias, Chapter 25, pp. 459–476 (1995).
Feld, Gregory K., et al. "Radio frequency Catheter Ablation for the Treatment of Human Type–1 Atrial Flutter," Ciculation, vol. 86, No. 4, pp. 1223–1240 (Oct., 1992).
Sauodi, N. et al. "Catheter Ablation of the Atrial Myocardium in Human Type–I Atrial Flutter," Circulation, vol. 81, No. 3, pp. 762–771 (Mar., 1990).
Singer, I, et al., "Catheter Ablation for Arrhythmias," Clinical Manual of Electrophysiology, pp. 421–431 (1993).
Falk, R.H., et al. "Atrial Fibrillation, Mechanisms and Management," pp. 359–374 (1992).
Horowitz, L.N. "Current Management of Arrhythmias," pp. 373–378 (1991).
Gallagher, J.J. et al. "Catheter Technique for Closed Chest Ablation of the Atrioventricular Conduction System," N. Engl. J. Med., vol. 306, pp. 194–200 (1982).
Tracy, C.M. "Radiofrequency Catheter Ablation of Ectopic Atrial Tachycardia Using Paled Activation Sequence Mapping," J.Am. Coll. Cardiol., vol. 21, pp. 910–917 (1993).
Saul, J.P. et al. "Catheter Ablation of Accessory Atroventricular Pathways in Young Patients: Use of Long Vascular Sheaths, the Transseptal Approach and a Retrograde Left Posterior Parallel Approach" J. Amer. Coll. Card., vol. 21, No. 3, pp. 571–583 (1993).
Swartz, J.F. et al. "Radiofrequency Endocardial Catheter Ablation of Accessory Atrioventricular Pathway Atrial Insertion Sites" Circulation, vol. 87, No. 2, pp. 487–499 (1993).

Primary Examiner—Max Hindenburg
Assistant Examiner—Pamela L. Wingood
Attorney, Agent, or Firm—Scott R. Cox

[57] ABSTRACT

A guiding introducer system for use in the right atrium comprised of an inner guiding introducer and an outer guiding introducer wherein the inner guiding introducer is comprised of a first and second section and the outer guiding introducer is comprised of a first, second and third section. The guiding introducer system is for use in sensing, pacing, and ablating procedures within the right atrium of the human heart.

8 Claims, 5 Drawing Sheets

GUIDING INTRODUCERS & CATHETER
IN
RIGHT ATRIUM

1) TRICUSPID VALVE
2) INNER GUIDING INTRODUCER
3) CATHETER
4) OUTER GUIDING INTRODUCER

GUIDING INTRODUCER SYSTEM FOR USE IN THE RIGHT ATRIUM

This application is a division of application Ser. No. 08/333,759, filed Nov. 3, 1994, now U.S. Pat. No. 5,628,316, which application is a continuation-in-part of application Ser. No. 08/146,744, filed Nov. 3, 1993, now U.S. Pat. No. 5,427,119.

BACKGROUND OF THE INVENTION

1. Field of Invention

This invention relates to introducers. More particularly, this invention relates to a guiding introducer system for use within the right atrium of the human heart.

2. Prior Art

Introducers and catheters have been in use for medical procedures for many years. For example, one use has been to convey an electrical stimulus to a selected location within the human body. Another use is the monitoring of measurements for diagnostic tests within the human body. Thus, catheters may be used by a physician to examine, diagnose and treat while positioned at a specific location within the body which are otherwise inaccessible without more invasive procedures. Catheters may be inserted into a major vein or artery which is near the body surface. The catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery, vein or body part while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to a desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,299,574, 5,215,540, 5,016,640 and 4,883,058 disclose catheters for use in selective coronary angiography of the right coronary artery. See also U.S. Pat. No. 4,033,5741. Finally, U.S. Pat. No. 4,898,591 discusses a catheter with inner and outer layers containing braided portions. The '591 patent also discloses a number of different curvatures for intravascular catheters.

In addition to single catheters with various curvatures, U.S. Pat. No. 4,581,017 discloses an inner and outer guide catheter, numbers 138 and 132, for use with a balloon catheter for treatment of coronary arteries. U.S. Pat. No. 5,267,982 discloses a catheter assembly and methods for catheterization of coronary arteries wherein an inner catheter (50) and outer catheter (52) are used in combination for the treatment of right and left coronary angiographic procedures. See also U.S. Pat. No. 4,935,017 which discloses a similar device. U.S. Pat. No. 5,290,229 discloses a straight outer sheath and a preformed inner catheter for use in the heart. See also U.S. Pat. Nos. 5,304,131, 5,120,323, 4,810,244 and 5,279,546.

Thus, there are a number of patents which disclose catheters with predetermined shapes, designed for use in specific medical procedures generally associated with the heart or the vascular system. Because of the precise physiology of the heart and the vascular system, catheters or introducers with carefully designed shapes for predetermined uses within the human heart and vascular system are important.

The sources of energy used for catheter ablation vary. Initially, high voltage, direct current (DC) ablation techniques were commonly used. However, because of problems associated with the use of DC current, radio frequency (R.F.) ablation has become a preferred source of energy for the ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. Other energy sources being considered for ablation of heart tissue include laser, ultrasound, microwave and direct current fulgutronization procedures. Also disclosed have been procedures where the temperature about the catherization probe is modified.

Catheter ablation of accessory pathways associated with Wolfe-Parkinson-White syndrome using a long vascular sheath by both a transseptal and retrograde approach is discussed in Saul, J. P., et al. "Catheter Ablation of accessory Atrioventricular Pathways in Young Patients: Use of long vascular sheaths, the transseptal approach and a retrograde left posterior parallel approach" *Journal of the American College of Cardiology*, Vol. 21, no. 3, pps. 571–583 (Mar. 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (February, 1993).

Accordingly, it is an object of this invention to prepare a dual guiding introducer system for selected medical procedures in the right atrium.

It is a further object of this invention to prepare a dual guiding introducer system for use in selected electrophysiology procedures within the right atrium of the heart.

Another object of this invention is to prepare a dual guiding introducer system for use in selected ablation procedures within the right atrium of the heart.

These and other objects are obtained by the design of the guiding introducer system disclosed in the instant invention.

SUMMARY OF INVENTION

The instant invention is a guiding introducer system for selected medical procedures in the right atrium. It is comprised of an inner guiding introducer and an outer guiding introducer. A dilator is preferably used with the guiding introducer system, which dilator may be a standard dilator used with conventional introducers. The inner guiding introducer is a shaped introducer comprised of a first and second section, wherein the first section is a generally elongated straight section which is merged at its distal end with the second section which is a simple curved section. The outer guiding introducer is comprised of a first, second and third sections, wherein the first section is a generally elongated straight section which is merged at its distal end with the second and third sections which form complex curved sections. The inner guiding introducer is longer than the outer guiding introducer to permit it to extend out from the lumen of the outer guiding introducer to form various curves and shapes.

DETAILED DESCRIPTION OF THE DRAWINGS

Figure 1:
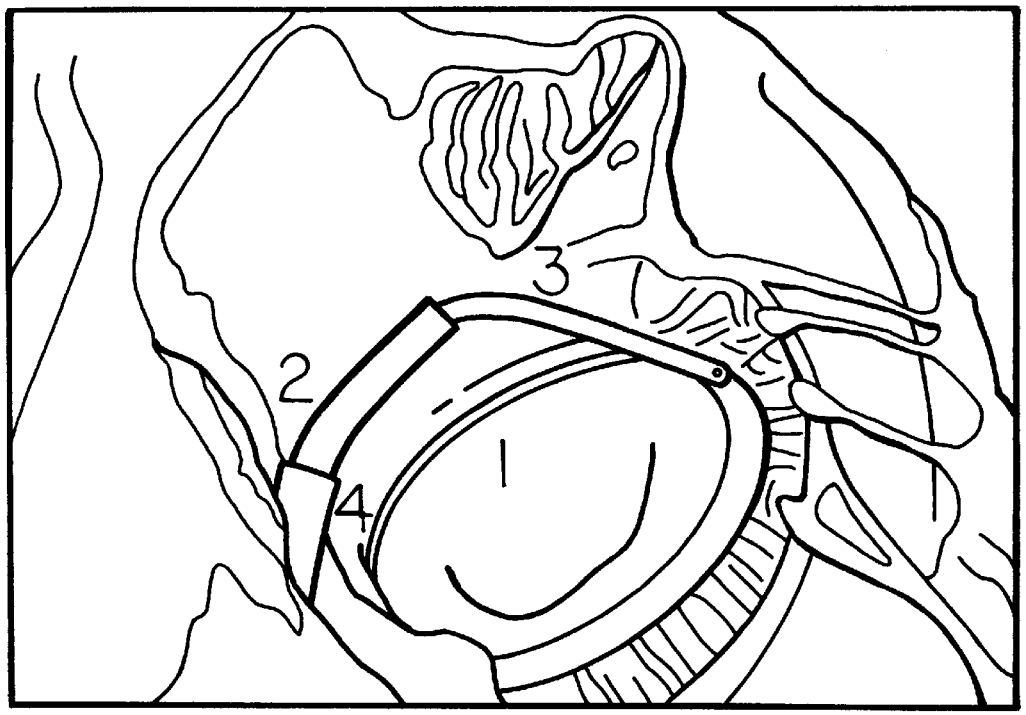
FIG. 1 is a cross-section of the right side of the heart showing the right atrium and the placement of the guiding introducer system.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a recessed portion, the fossa ovalis. See FIG. 1. In the heart of a fetus, the fossa ovalis is open, permitting the fetal blood to flow between the right and left atria. In most individuals, this opening closes after birth, but in as many as 25 percent of individuals an opening still remains in the fossa ovalis between the right and left atria. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electro-chemical signals pass sequentially through the myocardium from the atrial to the ventricular tissue along a well defined route which includes the His-Purkinje system. Initial electrical impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, a common arrhythmia is Wolfe-Parkinson-White syndrome (W-P-W). The cause of W-P-W is generally believed to be the existence of an anomalous conduction pathway or pathways that connects the atrial muscle tissue directly to the ventricular muscle tissue, thus by-passing the normal His-Purkinje system. These pathways are usually located in the fibrous tissue that connects the atrium and the ventricle. In recent years a technique has been developed to destroy these anomalous conduction pathways by delivering energy into the tissue in which the pathways exist. To accomplish this procedure a special electrode catheter is positioned as close as possible to the anomalous conduction pathway to maintain constant tissue contact while energy is delivered to the cardiac tissue to destroy the pathway. This same type of contact with the cardiac tissue is also necessary when mapping or other such procedures are employed relating to these pathways.

One end of these anomalous conduction pathways can be located either in the right atrium or in the left atrium with the other end of the pathway located in the corresponding ventricle. When the anomalous conduction pathway is located between the left atrium and the left ventricle, there are two approaches to positioning the catheter near the pathway for the appropriate medical procedure. One is to introduce the catheter into the femoral artery by a standard introducer sheath and advance it up the aorta, across the aortic valve into the left ventricle and then attempt to position its tip under the mitral valve annulus near the anomalous conduction pathway. This approach is frequently difficult for many reasons, including the structure of the left ventricle, the fact that it requires arterial access and potential problems associated with ablation of ventricular tissue including the possibility of creation of a substrate for a future arrhythmia which could result in sudden cardiac death. The other approach is to introduce a transseptal sheath apparatus, a long single plane curve introducer, into the right femoral vein and advance it through the inferior vena cava into the right atrium. A puncture is then made through the fossa ovalis in the interatrial septum and the apparatus is advanced into the left atrium where the trocar and dilator of the apparatus are removed, leaving the introducer in position in the left atrium. The mapping or ablation catheter is then inserted through the introducer and into the left atrium and positioned on top of the mitral valve annulus near the anomalous conduction pathway. Specific positions may be chosen for the mapping or ablation on the left side of the heart, including specifically posteroseptal, posterior, posterolateral, lateral and anterolateral positions around the mitral valve annulus.

Traditionally, there have been two techniques for locating and ablating anomalous conduction pathways which are situated between the right atrium and right ventricle. Either method can be initiated by advancing a catheter through an access site into a vein in the leg, neck or upper chest.

The first technique, which approaches the pathway from the pathway's ventricular insertion site, involves entering the right atrium from either the inferior or superior vena cava, passing through the tricuspid valve, and advancing toward the apex of the right ventricle. Then the catheter is directed to make a 180 degree turn to reverse its path back up toward the right atrium and locate the accessory pathway under the tricuspid valve apparatus. The accessory pathway is then ablated from the ventricular insertion site under the tricuspid valve.

The second technique, which approaches the pathway from the atrial insertion site, is to enter the right atrium from the inferior or superior vena cava, and attempt to locate the atrial insertion site of the accessory pathway around the tricuspid valve annulus. The accessory pathway is then ablated from the pathway's atrial insertion site on the atrial aspect of the tricuspid valve.

AV nodal pathways can be located and ablated from the right atrium.

Mere introduction of the catheter into the right atrium is not sufficient to effectively and efficiently perform these medical procedures, especially the mapping or ablation of the anomalous conduction pathways. These medical procedures are usually performed using a specific catheter. The medical practitioners monitor the introduction of the catheter and its progress through the vascular system by a fluoroscope. However, such fluoroscopes do not easily identify the specific features of the heart in general and the critically important structures of the right atrium in specific, thus making placement of the catheter difficult. This placement is especially difficult as the beating heart is in motion and the catheter will be moving within the right atrium as blood is being pumped through the heart throughout the procedure. The structure and shape of the guiding introducer of the instant invention addresses and solves these problems.

Figure 2:
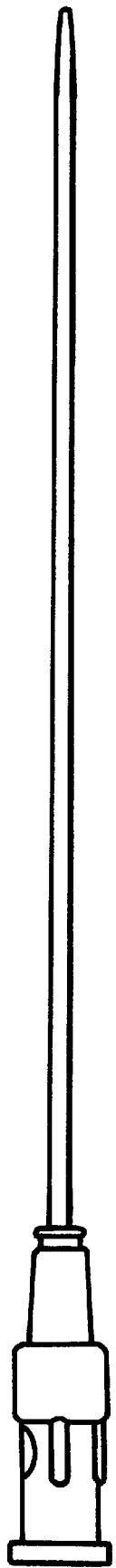
FIG. 2 is a perspective view of the dilator.
Figure 5:
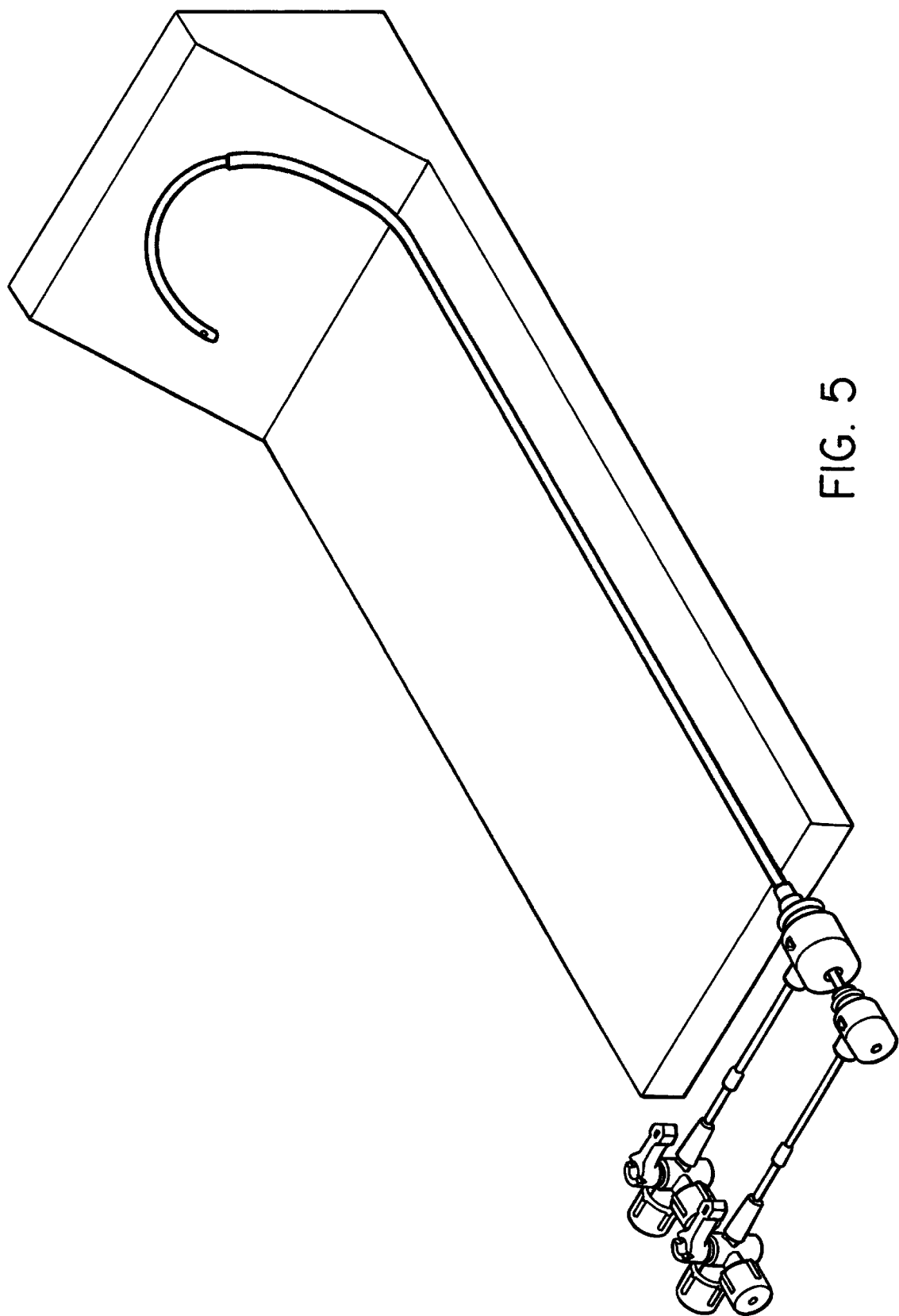
FIG. 5 is a perspective view of the inner and outer guiding introducers in combination with the distal end of the inner guiding introducer extended from the distal end of the outer guiding introducer.

The dual guiding introducer system for use in the right atrium is comprised of an inner and an outer guiding introducer. See FIG. 5. A dilator is also preferably used wherein the dilator is preferably a conventional dilator used with cardiac procedures and is not generally curved. See FIG. 2. The standard length of the dilator is about 60 to about 80 cm.

Figure 3:
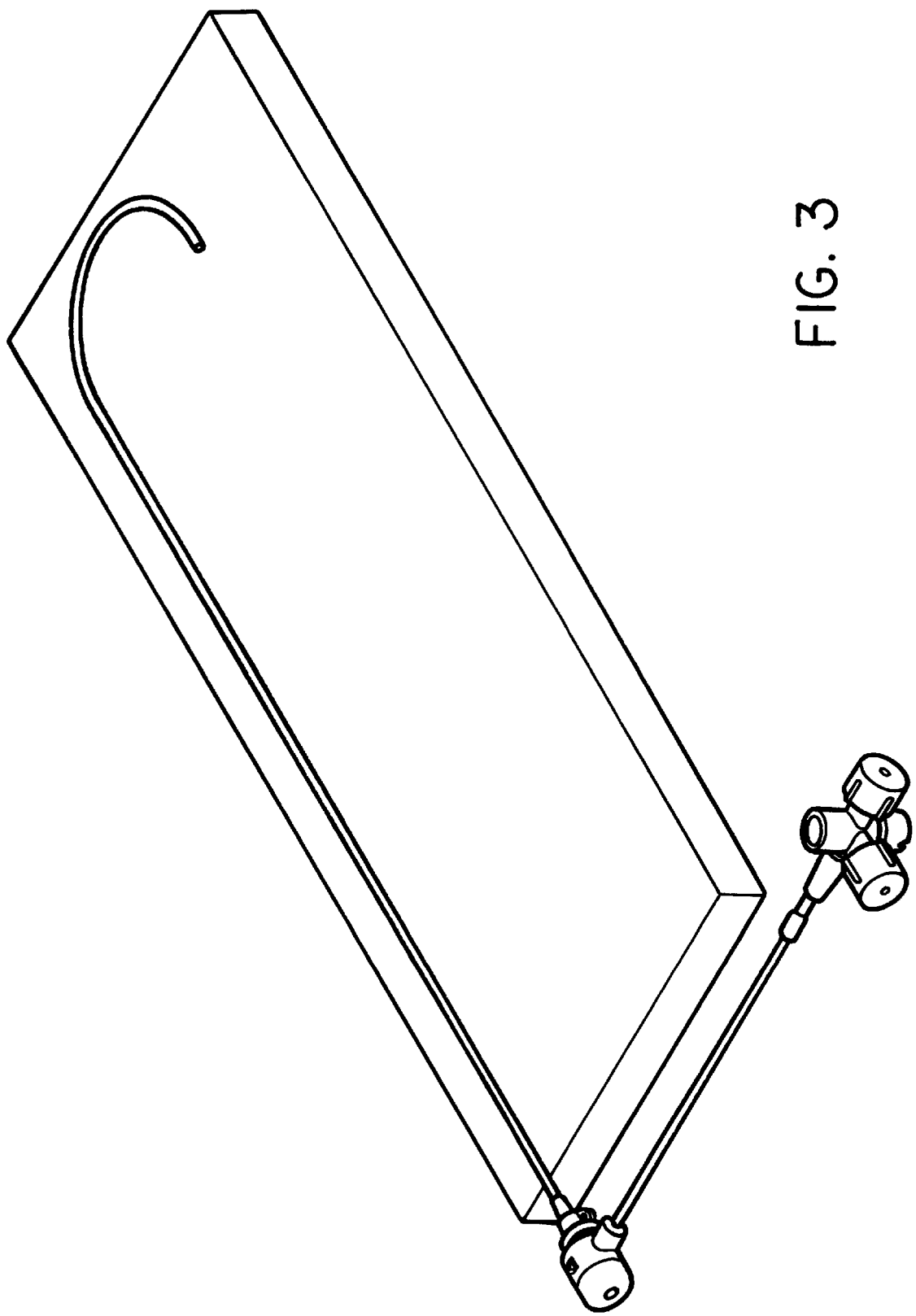
FIG. 3 is a perspective view of the inner guiding introduce.

The inner guiding introducer is generally comprised of two sections. See FIG. 3. The first section is a conventional generally elongated hollow straight catheter section of sufficient length for introduction into the patient and for manipulation from the point of insertion to the specific desired location within the heart. Merged with the distal end of the first section of the guiding introducer, but an integral part of the entire guiding introducer, is the second section which is a curved section, curved in a simple curve with a radius of about 0.5 to about 2.0 in., preferably about 0.7 to about 1.3 in. to form an arc of approximately 150 to about 270 degrees, preferably about 170 to about 190 degrees ending in a distal tip.

Figure 4:
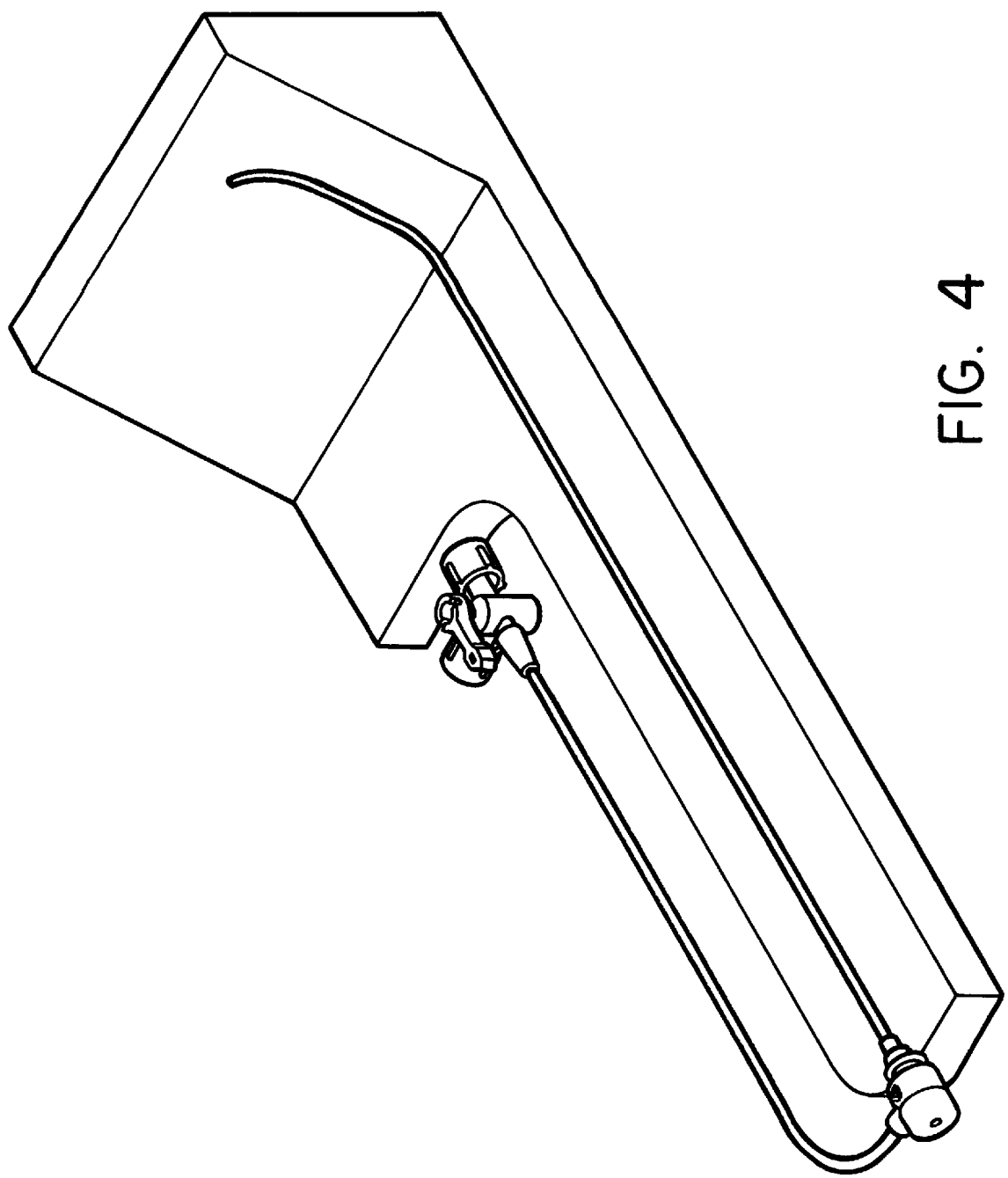
FIG. 4 is a perspective view of the outer guiding introducer.

The outer guiding introducer for use in the right atrium is comprised of a first, second and third section. See FIG. 4. (As with the inner guiding introducer, this division into three separate sections is for ease of illustration. The guiding introducer is preferably formed in a single procedure with each section an integral part of the overall guiding introducer.) The first section is a conventional, generally elongated hollow straight catheter section of sufficient length for introduction into the patient and for manipulation from the point of insertion to the specific desired location within the heart. Merged with the distal end of the first section of the guiding introducer is the second section which is comprised of a curved section and a straight section, wherein the curved section curves upward as shown in FIG. 4 in a longitudinal curve with a radius from about 0.25 to about 0.75 cm., preferably about 0.4 to about 0.6 in. to form an arc of approximately 40 to about 60 degrees, preferably about 45 to about 55 degrees. Merged with the distal end of this curve is the straight section from about 0.4 to about 0.7 in. in length, preferably about 0.55 to about 0.65 in. in length. At the distal end of the second section is the third section. The third section is comprised of a curved section with a radius of about 0.5 to about 1.5 in. and preferably about 0.8 to about 1.2 in. with an arc of about 30 to about 60 degrees, and preferably about 35 to about 55 degrees, which ends in the distal tip of the outer guiding introducer. The curved section of the third section curves in approximately the same plane as the curve of the second section (within about 15 degrees of coplanar).

By extending the distal tip of the inner guiding introducer away from the distal tip of the outer guiding introducer and by rotating the inner guiding introducer with respect to the outer guiding introducer, a variety of shapes of the overall guiding introducer system are formed to direct a mapping and/or ablation catheter toward the site within the atrium of interest. See FIG. 5. These shapes permit ablation procedures within the right atrium to be performed, for example, postero septal and septal accessory pathways. By further extension of the inner guiding introducer, accessory pathways located anterioseptal to anterior can be treated. Further extension of the inner guiding introducer within the outer guiding introducer permits analysis of treatment of anterior to anteriolateral accessory pathways. By further extension, treatment is available for accessory pathways located anterolateral to lateral to the tricuspid valve annulus. In addition, by manipulation of the inner guiding introducer within the outer guiding introducer, additional procedures can be performed within the right atrium, for example, for treatment of ectopic atrial tachycardia or even for certain atrial fibrillation procedures. Being able to extend the inner guiding introducer within the outer guiding introducer and to rotate the inner guiding introducer within the outer guiding introducer permits a wide variety of overall shapes which is particularly useful to medical practitioners. The medical practitioner is able to determine the relative location of the inner and outer guiding introducers because of tip markers located near the distal tip of both the inner and outer guiding introducers.

The distal tip of both the inner and outer guiding introducers may be, and generally will be, tapered to form a good transition with the dilator.

The relative size of the outer guiding introducer in relation to the inner guiding introducer should be sufficient to permit the inner guiding introducer to be torqued or rotated within the outer guiding introducer without undue restriction on such movement. Preferably, the difference in size between the inner and outer guiding introducer should be at least about 3 "French" (1 French equals about one-third of a millimeter). For example in one preferred embodiment, the outer guiding introducer is 11 French in size and the inner guiding introducer is 8 French. By this difference in diameter, there is approximately 1 French unit of volume between the outer surface of the inner guiding introducer and the inner surface of the outer guiding introducer. Preferably, this volume of space between the inner and outer guiding introducer is filled with a biocompatible solution, such as a saline solution, preferably a heparinized saline solution. This saline solution also provides lubricity to the two introducers, allowing more accurate torquing of the enhanced inner guiding introducer within the outer guiding introducer. In addition, it is preferable that the structure of both the inner and the outer guiding introducer have a high torsional constant to allow for the full utilization of the various shapes available by rotation and extension of the inner and outer guiding introducer. To permit this high torsional constant, in one preferred embodiment the inner guiding introducer is braided to provide further strength and structural stability.

The guiding introducer may be made of any material suitable for use in humans, which has a memory or permits distortion from and subsequent substantial return to the desired three dimensional or complex multi-planar shape. For the purpose of illustration and not limitation, the internal diameter of the tip of the guiding introducers may vary from about 6 to about 10 "French" Such introducers can accept dilators from about 6 to about 10 French and appropriate guidewires. Obviously if larger, or smaller dilators and catheters are used in conjunction with the guiding introducers of the instant invention, modification can be made in the size of the instant guiding introducers.

The pair of guiding introducers preferably contain one or a multitude of radiopaque tip marker bands near the distal tip of the guiding introducers. Various modifications may be made in the shapes by increasing or decreasing its size or adding additional tip markers.

The inner and outer guiding introducers also preferably contain one or a plurality of vents near the distal tip of the guiding introducers, preferably 3 or 4 or such vents. The vents are preferably located no more than about 5 to 6 cm. from the tip of the guiding introducers and more preferably 0.5 cm. to about 4.0 cm. from the tip. The size of these vents should be in the range of about 20 to 60 $\frac{1}{1000}$ of an inch in diameter. These vents are generally designed to prevent air embolisms from entering the guiding introducers caused by the withdrawal of a catheter contained within the guiding introducers in the event the distal tip of the guiding introducers is occluded. For example, if the tip of the inner guiding introducer is placed against the myocardium and the catheter located within the inner guiding introducer is withdrawn, a vacuum may be created within the inner guiding introducers if no vents are provided. If such vacuum is formed, air may be forced back into the guiding introducer by the reintroduction of a catheter into the lumen of the guiding introducers. Such air embolism could cause problems for the patient including the possibility of a stroke, heart attack or other such problems common with air embolism in the heart. The addition of vents near the distal tip of the guiding introducers prevents the formation of such vacuum by permitting fluid, presumably blood, to be drawn into the lumen of the guiding introducers as the catheter is being removed, thus preventing the possibility of formation of an air embolism.

Variances in size or shape of the pair of guiding introducer are also intended to encompass pediatric uses for the pair of guiding introducers of the instant invention, although the preferred use is for adult human hearts. It is well recognized that pediatric uses may require reductions in size of the various sections of the guiding introducers in particular the first section, but without any significant modification to the shape or curves of the guiding introducers. However, because incremental changes can be made in the overall shape of the pair of guiding introducers, the system can better adjust to differing shapes and sizes of heart than can a single guiding introducer.

In operation, a modified Seldinger technique is normally used for the insertion of a catheter into either an artery or vein of the body. Using this procedure, a small skin incision is made at the appropriate location to facilitate the catheter and dilator passage. The subcutaneous tissue is then dissected, followed by a puncture of the vessel with an appropriate needle with stylet positioned at a relatively shallow angle. The needle is then partially withdrawn and reinserted at a slightly different angle into the vessel, making sure that the needle remains within the vessel. A soft flexible tip of an appropriate sized guidewire is then inserted through and a short distance beyond the needle into the vessel. Firmly holding the guidewire in place, the needle is removed. The guidewire is then advanced through the vessel into the inferior vena cava or the right atrium. With the guidewire in place, either in the inferior vena cava or into the right atrium, the dilator is then placed over the wire with the pair of guiding introducers placed over the dilator. The dilator and pair of guiding introducers generally form an assembly to be advanced together along the guidewire into the inferior vena cava or into the right atrium. The guidewire is then withdrawn as is the dilator, leaving the pair of guiding introducers either in the inferior vena cava or in the right atrium. If the pair of guiding introducers has been left in the inferior vena cava, it is then advanced up the inferior vena cava into the right atrium. By extending and withdrawing the inner guiding introducer from the outer guiding introducer and by rotating the inner guiding introducer within the outer guiding introducer, great variances in the overall shape of the guiding introducer system can be achieved.

By movement of the inner guiding introducer within the outer guiding introducer in conjunction with fluoroscopic viewing, the distal portion of the outer guiding introducer can be manipulated to direct the distal end of a catheter placed within the lumen of the inner guiding introducer to a specific internal surface within the right atrium. See FIG. 5. In addition, by providing sufficient rigidity, the distal end of the inner guiding catheter can be maintained in that fixed location or surface position of the endocardial structure to permit the appropriate procedures to be performed. If sensing procedures are involved, the pair of guiding introducers is placed in the desired location. At that point, the electrical activity of the heart peculiar to that location can be precisely determined by use of an electrophysiology catheter placed within the guiding introducer. Further, as the pair of guiding introducers permit precise location of catheters, an ablation catheter may be placed at a precise location for destruction of the cardiac tissue by the use of energy, for example, radio frequency, thermal, laser or direct current (high energy direct, low energy direct and fulgutronization procedures). The precise placement of the ablation catheter tip on the cardiac tissue is important as there will be no dilution of the energy delivered due to unfocused energy being dissipated over the entire cardiac chamber and lost in the circulating blood by a constant movement of the tip of the ablating catheter. This permits a significantly reduced amount of energy to be applied, while still achieving efficient ablation. Further, time used to perform the procedure is significantly reduced over procedures where no guiding introducers are used.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A guiding introducer system to be used in the right atrium of a human heart comprising a precurved cardiac chamber inner guiding introducer and a precurved cardiac chamber outer guiding introducer wherein said guiding introducers are used in combination in a chamber of the heart whereby the guiding introducers are structurally stabalized to enhance their rigidity to assist in the control of their movement within the chamber of the heart.

2. The guiding introducer system of claim 1 further comprising a dilator, wherein said dilator is generally straight.

3. The guiding introducer system of claim 1 wherein the inner guiding introducer comprises a first and second section each with proximal and distal ends, wherein the first section is a generally elongated straight section, wherein merged with the distal end of said first section is the second section which is a curved section with a radius of about 0.5 to about 1.5 in. to form an arc of approximately 150 to 270 degrees ending in the distal end of the second section of the inner guiding introducer.

4. The guiding introducer system of claim 1 wherein the outer guiding introducer comprises, a first, second and third section, each with distal and proximal ends, wherein the first section is a generally elongated straight section, wherein merged with the distal end of said first section is the second section which comprises a curved portion and a straight portion, wherein the curved portion has a radius of about 0.25 in. to about 0.75 in. to form an arc of about 40 to 60 degrees, wherein the straight portion of the second section is from about 0.4 to about 0.7 in. in length, wherein merged with the distal end of the second section is the third section, wherein said third section comprises a curved portion with a radius of about 0.5 to about 1.5 in. to form an arc of about 30 to about 60 degrees and wherein the third section is generally coplanar with the second section ending in the distal end of the third section of the outer guiding introducer.

5. The guiding introducer system of claim 3 wherein a plurality of vents is provided near the distal end of the second section of the inner guiding introducer.

6. The guiding introducer system of claim 4 wherein a plurality of vents is provided near the distal end of the third section of the outer guiding introducer.

7. The guiding introducer system of claim 3 wherein tip markers are contained within the inner guiding introducer.

8. The guiding introducer system of claim 4 wherein tip markers are contained within the outer guiding introducer.

* * * * *